United States Patent [19]

Lu et al.

[11] Patent Number: 4,654,175
[45] Date of Patent: Mar. 31, 1987

[54] ORGANIC SULFATE AND SULFONATE COMPOSITIONS

[75] Inventors: Chin H. Lu, Webster, N.Y.; Seymour Baron, Wayne, N.J.

[73] Assignee: Xerox Corporation, Stamford, Conn.

[21] Appl. No.: 377,540

[22] Filed: May 12, 1982

[51] Int. Cl.$^4$ .............................................. C07C 87/30
[52] U.S. Cl. .................................. 260/501.15; 558/27
[58] Field of Search ............... 260/501.15, 457, 459 A

[56] References Cited

U.S. PATENT DOCUMENTS

| | | | |
|---|---|---|---|
| 3,392,186 | 7/1968 | Lynn | 260/457 |
| 3,636,114 | 1/1972 | Tobler et al. | 260/457 |
| 3,708,527 | 1/1973 | Duennenberger et al. | 260/501.15 |
| 3,893,935 | 7/1975 | Jadwin et al. | 252/62.1 |
| 3,898,284 | 8/1975 | Bauman | 260/501.15 |
| 3,914,496 | 10/1975 | Jorek et al. | 260/501.15 |
| 4,060,652 | 11/1977 | Borisov et al. | 260/501.15 |
| 4,298,672 | 11/1981 | Lu | 430/108 |
| 4,323,634 | 4/1982 | Jadwin | 430/110 |
| 4,338,390 | 7/1982 | Lu | 430/106 |

FOREIGN PATENT DOCUMENTS 745648 11/1966 Canada ............................. 260/501.15
2014276 3/1970 Fed. Rep. of Germany .

OTHER PUBLICATIONS

Luca et al., Chem. Abst., 84, 142,496z (1976).
Ibid., 83, 107,691s (1974).

Primary Examiner—Nicky Chan
Attorney, Agent, or Firm—E. O. Palazzo

[57] ABSTRACT

This invention is generally directed to new organic sulfate and organic sulfonate compositions and processes for the preparation of such compositions. These compositions are of the following formula

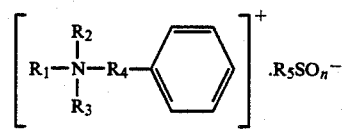

wherein $R_1$ is an alkyl group containing from about 12 carbon atoms to about 22 carbon atoms, $R_2$ and $R_3$ are independently selected from alkyl groups containing from about 1 carbon atom to about 5 carbon atoms, $R_4$ is an alkylene group containing from about 1 carbon atom to about 5 carbon atoms, $R_5$ is a para substituted phenyl group wherein the substituent is an alkyl group containing from about 1 carbon atom to about 6 carbon atoms, or an alkyl group containing from about 1 carbon atom to about 3 carbon atoms, and n is the number 3 or 4.

1 Claim, No Drawings

ORGANIC SULFATE AND SULFONATE COMPOSITIONS

BACKGROUND OF THE INVENTION

This invention is generally directed to new organic sulfate and sulfonate compositions and process for the preparation of such compositions. More specifically the present invention is directed to certain toluene sulfonate and sulfate compositions which are useful as charge enhancing additives for electrostatographic developer compositions comprised of toner particles and carrier particles. Thus, for example, toner compositions containing the sulfates and sulfonates of the present invention are useful in electrostatographic imaging systems wherein the imaging member is charged negatively, and further such compositions are useful in imaging systems containing a Viton fuser roll as more specifically detailed hereinafter.

Described in a copending application U.S. Ser. No. 212,969, filed Dec. 4, 1980, are toner compositions containing the organic sulfate and sulfonate compounds of the present invention. The disclosure of the copending application is totally incorporated herein by reference.

Various sulfate and sulfonate compositions are known including, for example, ammonium lauryl sulfate, sodium xylene sulfonate, sodium dodecyl benzene sulfonate, triethanol amine dodecyl benzene sulfonate, cetyl trimethyl ammonium para-toluene sulfonate, sodium tetradecyl sulfate, and the like. These materials are, for example, useful as surfactants, anti-static additives for toiletry preparations, and the like. There continues to remain a need, however, for new sulfates and sulfonates, particularly those which are useful as charge enhancing additives. The need for these additive, especially those which impart a positive charge to the toner resin has experienced a recent growth in view of the desire to use negatively charged photoresponsive imaging devices in electrostatic imaging systems.

Various charge control additives are disclosed in the prior art, thus for example, there is disclosed in U.S. Pat. No. 3,893,935 the use of certain quaternary ammonium compounds as charge control agents for electrostatic toner compositions. According to the disclosure of this patent, certain quaternary ammonium compounds when incorporated into toner materials were found to provide a toner composition which exhibited relatively high uniform and stable net toner charge when mixed with a suitable carrier vehicle. A similar teaching is contained in U.S. Pat. No. 4,079,014 wherein a diazo toner charge control additive is described. Further, there is disclosed in U.S. Pat. No. 4,298,672 as charge enhancing additives alkyl pyridinium compositions including cetyl pyridinium chloride.

Many of the above disclosed charge control materials interact with certain fuser rolls, such as Viton fuser rolls, used in electrostatographic systems. This interaction causes these fuser rolls to be adversely affected, resulting ultimately in a deterioration of image quality. For example, the Viton fuser rolls discolor and turn black, as well as develop multiple surface cracks when certain charge control additive compounds are employed in the toner mixture.

One Viton fuser roll selected for electrostatographic devices, particularly xerographic imaging systems, is comprised of a soft roll fabricated from lead oxide and duPont Viton E-430 resin (a vinylidene fluoride, hexafluoropropylene copolymer). This roll can be prepared by blending together, and curing at elevated temperatures approximately 15 parts of lead oxide, and 100 parts of Viton E-430. Apparently the function of the lead oxide is to generate unsaturation by dehydrofluorination for cross-linking, and to provide release mechanisms for the toner compositions. Excellent image quality has been obtained with the use of Viton fuser rolls, however, in some instances, there is a toner-fuser compatibility problem when charge control substances are contained in the toner mixture. It appears that certain charge control additive, such as quaternary ammonium compounds, and alkyl pyridinium compounds react with the Viton fuser roll. For example, cetyl pyridinium chloride when part of the toner mixture appears to be catalytically decomposed by the lead oxide in the fuser roll, resulting in a highly unsaturated compound, which polymerizes and condenses with the unsaturated Viton. As a result, the Viton fuser turns black and develops multiple surface cracks, thereby resulting in image quality deterioration.

SUMMARY OF THE INVENTION

It is an object of the present invention to provide novel organic sulfate and organic sulfonate compositions and processes for the preparation of such compositions.

A further object of the present invention is to provide organic sulfonate compositions containing a nitrogen atom therein.

In yet another object of the present invention there is provided organic sulfate compositions containing a nitrogen atom therein.

In a further object of the present invention there is provided certain organic sulfonates and sulfate compositions which contain a positively charged portion and a negatively charged portion.

These and other objects of the present invention are accomplished by the provision of organic sulfates and sulfonates of the following formula:

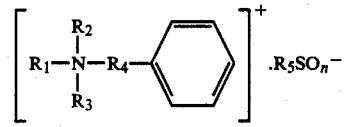

wherein $R_1$ is an alkyl group containing from about 12 carbon atoms to about 22 carbon atoms, and preferably from about 14 carbon atoms to about 18 carbon atoms, $R_2$ and $R_3$ are independently selected from alkyl groups containing from about 1 carbon atom to about 5 carbon atoms, $R_4$ is an alkylene group containing from about 1 carbon atom to about 5 carbon atoms, $R_5$ is a para substituted phenyl group wherein the Substituent is an alkyl group containing from about 1 to about 5 carbon atoms, such as a tolyl group, or an alkyl group containing from about 1 carbon atom to about 3 carbon atoms, and n is the number 3, sulfonate, or 4, sulfate.

With further reference to the above formula, illustrative examples of alkyl groups include methyl, ethyl, propyl, butyl, pentyl, hexyl, octyl, nonyl, decyl, myristyl, cetyl, olely, pentadecyl, heptadecyl, stearyl and the like. Preferred alkyl groups for $R_1$ include myristyl, stearyl, and cetyl, while the preferred alkyl groups for $R_2$, $R_3$, and $R_5$ include methyl, ethyl and propyl. The preferred alkylene groups for $R_4$ are methylene and ethylene. Examples of other alkylene groups include propylene, butylene, pentylene and the like.

Illustrative examples of organic sulfate, and sulfonate materials of the present invention include stearyl dimethyl benzyl ammonium para-toluene sulfonate, stearyl dimethyl benzyl ammonium methyl sulfate, stearyl dimethyl phenethyl ammonium methyl sulfate, stearyl dimethyl phenethyl ammonium para-toluene sulfonate, phenethyl dodecyl dimethyl ammonium para-toluene sulfonate, benzyl hexadecyl ammonium para-toluene sulfonate, phenethyl stearyl dimethyl ammonium4-propyl phenyl sulfonate, cetyl diethyl benzyl ammonium methyl sulfate, myristyl dimethyl phenethyl ammonium para-toluene sulfonate, cetyl dimethyl benzyl ammonium methylsulfate, and the like.

The compositions of the present invention are prepared by, for example, reacting under suitable reaction conditions, the appropriate alkyl tosylate when the sulfonate compound is desired, or the appropriate sulfate, when the sulfate compound is desired with a suitable amine. The reaction conditions are generally similar for obtaining either the sulfate or the sulfonate. Further, generally, the reactions are accomplished in the presence of suitable solvents, such as ethyl acetate, methyl ethyl ketone, and the like.

The organic sulfonates can thus be prepared by reacting the appropriate organic sulfur containing compound with a tertiary amine in accordance with the following equation, wherein the substituents $R_1$, $R_2$, $R_3$ and $R_4$ are as defined herein, and $R_5$ is a para substituted phenyl group, wherein the substiuent is an alkyl group containing from about 1 carbon atom to about 6 carbon atoms, such as a tolyl group:

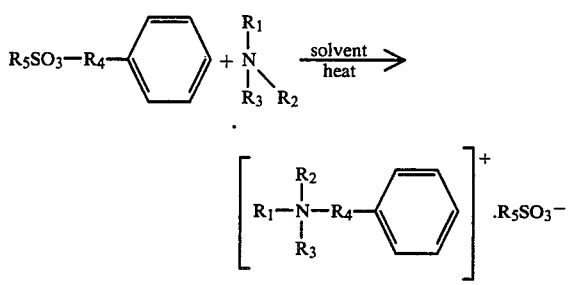

Illustrative examples of organic sulfur compound reactants selected for the preparation of the sulfonates include phenethyl tosylate, benzyl tosylate, other known tosylates, and the like, while examples of tertiary amine reactants include stearyl dimethyl amine, dodecyl dimethyl amine, and the like.

The organic sulfates are prepared in a similar manner wherein the appropriate sulfate is reacted with a tertiary amine. Thus, for example, stearyl dimethyl phenethyl ammonium methyl sulfate is prepared by reacting dimethyl sulfate with phenethyl stearyl methyl amine in the presence of a solvent, and heat.

Generally, the reactants are mixed together in equimolar ratios in the presence of from about 800 milliliters to about 1,500 milliliters of solvent, such as ethyl acetate, methyl ethyl ketone or similar solvents. Other solvent amounts can be selected provided the objectives of the present invention are achieved, thus, less than 800 milliliters, or more than 1,500 milliliters of solvent can be used. The reaction is generally accomplished at elevated temperatures, that is a temperature exceeding 65° C., and generally at a temperature of from 80° C. to 90° C., until the reaction has been completed as evidenced by the disappearance of the tertiary amine. Subsequently, the reaction mixture is cooled to room temperature, subjected to filtration and washing with a solvent used in the initial reaction. The washed product is then allowed to dry at room temperature, and the desired product is obtained, which product is identified by analyzing for the presence of the cation with sodium tetraphenyl boron, and/or elemental carbon, hydrogen, oxygen, nitrogen, sulfur analysis.

Numerous known methods may be selected for preparing toner compositions and developer compositions containing the sulfate, or sulfonate compositions of the present invention. These materials when present in the toner or developer compositions, function as charge enhancing additives in that they impart a positive charge to the toner resin. One method for preparing the toner composition involves melt blending resin particles, and pigment particles coated with the organic sulfate or organic sulfonate of the present invention, followed by mechanical attrition. Other methods include those well known in the art such as spray drying, melt dispersion, dispersion polymerization and suspension polymerization. In dispersion polymerization a solvent dispersion of a resin pigment in the organic sulfate or sulfonate composition of the present invention are spray dried under controlled conditions, thereby resulting in the desired toner composition, which product contains a positively charged toner in relationship to the carrier materials.

While any suitable resin may be selected for the toner composition, typical of such resins are polyamides, epoxies, polyurethanes, vinyl resins, and polyesters, especially those prepared from dicarboxylic acids and diols comprising diphenols. Any suitable vinyl resin may be selected including homopolymers or copolymers of two or more vinyl monomers. Typical of such vinyl monomeric units include: styrene, p-chlorostyrene, vinyl naphthalene, ethylenically unsaturated mono-olefins such as ethylene, propylene, butylene, isobutylene and the like; vinyl halides such as vinyl chloride, vinyl bromide, vinyl fluoride, vinyl esters such as vinyl acetate, vinyl propionate, vinyl benzoate, vinyl butyrate and the like; esters of alphamethylene aliphatic monocarboxylic acids such as methyl acrylate, ethyl acrylate, n-butylacrylate, isobutyl acrylate, dodecyl acrylate, n-octyl acrylate, 2-chloroethyl acrylate, phenyl acrylate, methylalpha-chloroacrylate, methyl methacrylate, ethyl methacrylate, butyl methacrylate and the like; acrylonitrile, methacrylonitrile, acrylamide, vinyl ethers such as vinyl methyl ether, vinyl isobutyl ether, vinyl ethyl ether, and the like; vinyl ketones such as vinyl methyl ketone, vinyl hexyl ketone, methyl isopropenyl ketone and the like; vinylidene halides such as vinylidene chloride, vinylidene chlorofluoride and the like; and N-vinyl indole, N-vinyl pyrrolidene and the like; and mixtures thereof.

Generally, toner resins containing a relatively high percentage of styrene are preferred. The styrene resin employed may be a homopolymer of styrene or styrene homologs of copolymers of styrene with other monomeric groups. Any of the above typical monomeric units may be copolymerized with styrene by addition polymerization. Styrene resins may also be formed by the polymerization of mixtures of two or more unsaturated monomeric materials with a styrene monomer. The addition polymerization technique employed embraces known polymerization techniques such as free radical, anionic, and cationic polymerization processes. Any of these vinyl resins may be blended with one or more resins if desired, preferably other vinyl resins, which insure good triboelectric properties and uniform resistance against physical degradation. However, nonvinyl type thermoplastic resins may also be employed including resin modified phenol formaldehyde resins, oil modified epoxy resins, polyurethane resins, cellulosic resins, polyether resins, and mixtures thereof.

Also esterification products of a dicarboxylic acid, and a diol comprising a diphenol may be used as a preferred resin material for the toner composition. These materials are illustrated in U.S. Pat. No. 3,655,374, the disclosure of which is totally incorporated herein by reference, the diphenol reactant being of the formula as shown in Column 4, beginning at line 5 of this patent, and the dicarboxylic acid being of the formula as shown in Column 6 of the above patent.

The toner resin is present in an amount in order that the total of all toner ingredients is equal to about 100 percent, thus when 5 percent by weight of the sulfonate or sulfate charge enhancing compound is present, and 10 percent by weight of a pigment or colorant, such as carbon black is present, about 85 percent by weight of resin material is present.

Any suitable pigment or dye may be selected as the colorant for the toner particles, such materials being well known and including for example, carbon black, magnetite, iron oxides, nigrosine dye, chrome yellow, ultramarine blue, duPont oil red, methylene blue chloride, phthalocyanine blue, and mixtures thereof. The pigment or dye should be present in the toner in sufficient quantity to render it highly colored, thus allowing the toner to form a clearly visible image on the recording member. For example, where conventional xerographic copies of documents are desired, the toner may comprise a black pigment, such as carbon black, or a black dye such as Amaplast black dye available from National Aniline Products, Inc. Preferably, the pigment is employed in amounts of from about 3 percent to about 50 percent by weight based on the total weight of the toner composition (toner resin, pigment, charge enhancing additive), however, if the pigment employed is a dye, substantially smaller quantities, for example, less than 10 percent by weight, may be used.

Various suitable carrier materials can be selected in formulating the developing compositions (toner plus carrier), as long as such carrier particles are capable of triboelectrically obtaining a charge of opposite polarity to that of the toner particles. In one embodiment, that would be a negative polarity, causing the toner particles to adhere to, and surround the carrier particles. Thus, the carrier particles are selected so that the toner particles acquire a charge of a positive polarity, and include materials such as sodium chloride, ammonium chloride, ammonium potassium chloride, Rochelle salt, sodium nitrate, aluminum nitrate, potassium chlorate, granular zircon, granular silicon, methylmethacrylate, glass, steel, nickel, iron ferrites, silicon dioxide and the like, with metallic carriers especially magnetic carriers being preferred. The carriers can be used with or without a coating. The coatings generally contain polyvinyl fluoride resins, but other resins especially those which charge negatively, such as polystyrene, halogen containing ethylenes and the like can be used. Many of the typical carriers that may be used are described in U.S. Pat. Nos. 2,638,552; 3,618,522; 3,533,835; and 3,526,533.

Also nickel berry carriers as described in U.S. Pat. Nos. 3,847,604 and 3,767,598 can be employed, these carriers being nodular carrier beads of nickel characterized by surface of reoccurring recesses and protrusions providing particles with a relatively large external area. The diameter of the coated carrier particle is from about 50 to about 1,000 microns, thus allowing the carrier to possess sufficient density and inertia to avoid adherence to the electrostatic images during the development process.

The carrier may be employed with the toner composition in any suitable combination, however, best results are obtained when about 1 part of toner composition is used to about 10 to about 200 parts by weight of carrier.

Toner compositions containing the sulfate, or sulfonate materials of the present invention are useful for causing the development of electrostatic latent images on most suitable electrostatic imaging surfaces capable of retaining charge, including conventional photoconductors, however, the toners of the present invention are best utilized in electrostatic systems wherein a negative charge resides on the photoreceptor surface, and this usually occurs with organic photoreceptors. Illustrative examples of such photoreceptors are polyvinyl carbazole, 4-dimethylaminobenzylidene, benzyhydrazide; 2-benzylidene-amino-carbazole, 4-dimethylaminobenzylidene, polyvinylcarbazole; (2-nitrobenzylidene)p-bromoaniline; 2,4-diphenyl-quinazoline; 1,2,4-triazine; 1,5-diphenyl-3-methyl pyrazoline 2-(4'dimethylamino phenyl)-benzoxazole; 3-amino-carbazole; polyvinylcarbazole-trinitrofluorenone charge transfer complex; phthalocyainines, layered photoresponsive devices as disclosed in U.S. Pat. No. 4,265,990, the disclosure of which is totally incorporated herein by reference, and the like.

In these imaging systems, the organic sulfate and sulfonate compositions of the present invention function as charge enhancing additives as indicated herein. Accordingly, the organic sulfonate and sulfates of the present invention impart a high positive charge to the toner resin. Generally, this is accomplished by incorporating the sulfate and sulfonate compounds in the toner composition in an amount of from about 0.1 percent by weight to about 10 percent by weight of the toner particles, and preferably from about 0.5 weight percent to about 5 weight percent. In one preferred embodiment, the organic sulfonate and sulfate compounds of the present invention are present in the toner composition in an amount of from 0.75 weight percent to about 3.0 weight percent. The sulfonate and sulfate materials of the present invention can either be blended into the toner resin or coated on the colorant or pigment used therein such as carbon black. When employed as a coating the materials of the present invention are present in an amount of from about 2 weight percent to about 20 weight percent, and preferably from about 5 weight percent to about 10 weight percent based on the weight of the pigment.

The following examples are being supplied to further define the species of the present invention, it being noted that these examples are intended to illustrate and not limit the scope of the present invention. Parts and percentages are by weight unless otherwise indicated.

EXAMPLE I

There was prepared the organic sulfonate stearyl dimethyl phenethyl ammonium para-toluene sulfonate by mixing in a 2 liter autoclave, 276 grams (1 gram mole) of phenethyl tosylate, 300 grams (1.01 gram moles) of stearyl dimethyl amine, and 1,000 milliliters of methylethyl ketone. The reaction mixture was then heated to a temperature of 86° C., and maintained at this temperature for 48 hours. Subsequently, the reaction mixture was cooled to a temperature of about 18°–20° C., and subjected to a filtration wherein the desired product was separated. This product was washed with 1,000 milliliters of methylethyl ketone and dried.

The product was identified by elemental carbon, hydrogen, oxygen, nitrogen, sulfur analysis, and by analyzing for the presence of the cation with sodium tetraphenyl boron, as stearyl dimethyl phenethyl ammonium para-toluene sulfonate of the following formula:

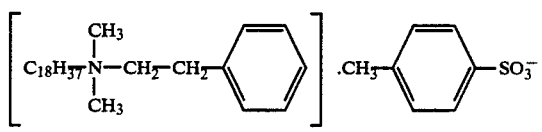

This compound had a melting point of about 75° C., and was non-hygroscopic.

EXAMPLE II

The procedure of Example I was repeated with the exception that 215 grams (1.01 gram moles) of dodecyl dimethyl amine was used in place of the stearyl dimethyl amine of Example I, and there resulted the sulfonate phenethyl dodecyl dimethyl ammonium para-toluene sulfonate.

EXAMPLE III

There was prepared benzyl stearyl dimethyl ammonium para-toluene sulfonate by mixing in a 2 liter flask 262 grams (1 gram mole) of a benzyl tosylate, 300 grams (1.01 gram moles) of stearyl dimethyl amine, and 1,000 milliliters of methylethyl ketone. The reaction was maintained at reflux under a nitrogen blanket for 16–20 hours. Subsequent to cooling the reaction mixture to room temperature, filtration was accomplished, and the resulting product was washed with methylethyl ketone and dried.

The isolated product was identified as benzyl stearyl dimethyl ammonium para-toluene sulfonate of the following formula:

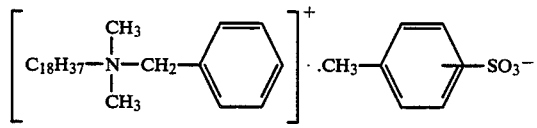

EXAMPLE IV

The procedure of Example III was repeated with the exception that 215 grams (1.01 gram moles) of dodecyl dimethyl amine was used in place of the 300 grams of the stearyl dimethyl amine of Example III and there was isolated hexadecyl dimethyl benzyl ammonium para-toluene sulfonate.

EXAMPLE V

There was prepared phenethyl stearyl dimethyl ammonium 4-propyl phenyl sulfonate by mixing in a 2 liter autoclave 304 grams (1.01 gram moles) of phenethyl 4-propyl benzene sulfonate, 300 grams of stearyl dimethyl amine, and 1,000 milliliters of methylethyl ketone. The reaction was then accomplished in accordance with Example I, and there was isolated after washing and filtration phenethyl stearyl dimethyl ammonium 4-propyl phenyl sulfonate.

The following examples relate to the preparation of toner compositions and developer compositions containing the organic sulfate and sulfonate compounds of the present invention.

EXAMPLE VI

A toner comprising 2 percent by weight of stearyl dimethyl benzyl ammonium para-toluene sulfonate, prepared in accordance with Example III, 6 percent of Regal ® 330, a carbon black, commercially available from Cabot Corporation, and 92 percent of a styrene/n-butylmethacrylate copolymer resin, 65/35, (65 percent by weight styrene and 35 percent by weight of n-butylmethacrylate), was prepared by melt blending followed by mechanical attrition. The resulting toner was classified in order to remove particles smaller than 5 microns in diameter.

The triboelectric charge of this toner was measured against a Hoeganese steel carrier coated with 0.15 percent Kynar 30, a vinylidene fluoride resin commercially available from Pennwalt Company, at 3 percent toner concentration with the following results:

| Time | Toner Tribo uc/g (microcoulombs per gram) |
|---|---|
| 10 minutes | +59 |
| 1 hour | +49 |
| 4 hours | +36 |
| 24 hours | +19 |

Charge distribution measurements showed that the above developer had a narrow charge distribution, with a minimum insignificant number, less than 1 percent of toner particles, containing a low charge, less than +15 uc/g, and minimum wrong sign negatively charged toner particles. Admix experiments showed that the toner had fast charging properties when fresh uncharged toner was added to the developer, that is, the fresh toner became positively charged in less than 1 minutes.

The above developer was also exposed to an atmosphere at 10 percent, 42 percent, and 80 percent relative humidity for 48 hours, and the triboelectric properties measured.

The triboelectric properties after 4 hours of roll milling varied only slightly at high and low relative humidity indicating the humidity insensitivity of this developer. The measurements were as follows:

| Relative Humidity Percentage | Toner Tribo at 4 hours uc/g (microcoulombs per gram) |
|---|---|
| 10 | +39 |
| 42 | +36 |
| 80 | +34 |

The above developer was used in a xerographic imaging device, containing an organic polyvinyl carbazole photoreceptor, charged negatively, which device also contained a Viton fuser roll. Not only were excellent high quality images obtained, but no damage occurred to the Viton fuser roll after 50,000 imaging cycles.

A sample of the stearyl dimethyl benzyl ammonium para-toluene sulfonate was placed on a part of a Viton fuser roll, lead oxide, duPont Viton E-430 resin, and heated to 205° C. for 30 minutes. The Viton fuser roll was then washed with alcohol to remove the compound and examined for discoloration and cracks. The Viton fuser roll did not discolor, nor turn black, nor were any surface cracks observed, indicating that this compound was compatible with the Viton fuser.

EXAMPLE VII

A toner composition comprised of 2 percent by weight of stearyl dimethyl benzyl ammonium para-toluene sulfonate prepared in accordance with Example III, 6 percent Regal ® 330 carbon black, and 92 percent of a styrene/butadiene copolymer resin (91/9), was prepared by melt blending followed by mechanical attrition. The resulting toner was classified to remove particles smaller than 5 microns in diameter. The classified toner was blended with the carrier described in Example VI, at 2.7 percent toner concentration. The triboelectric charge of the toner was measured with the following results:

| Time | Toner tribo uc/g (microcoulombs per gram) |
|---|---|
| 10 minutes | +83 |
| 1 hour | +53 |
| 3 hours | +43 |
| 5 hours | +35 |
| 24 hours | +15 |

EXAMPLE VIII

A toner comprising 2 percent by weight of stearyl dimethyl phenethyl ammonium para-toluene sulfonate prepared in accordance with Example I, 6 percent of Regal ® 330, a carbon black, and 92 percent by weight of a styrene/n-butadiene copolymer resin, 91/9, was prepared by melt blending followed by mechanical attrition. The resulting toner was classified to remove particles smaller than 5 microns in diameter. The classified toner was blended with the carrier of Example VI at 2.7 percent toner concentration. The triboelectric charge of this toner was measured with the following results:

| Time | Toner Tribo uc/g (microcoulombs per gram) |
|---|---|
| 10 minutes | +35 |
| 1 hour | +42 |
| 3 hours | +32 |
| 5 hours | +20 |
| 24 hours | +6 |

Charge distribution measurements showed that the above developer had a narrower charge distribution, with a minimum insignificant number, less than 1 percent of the toner particles, containing a low charge, less than +15 uc/g, and minimum wrong sign negatively charged toner particles. Admix experiments showed that the toner had fast charging properties when fresh uncharged toner was added to the developer, that is, the fresh toner became positively charged in less than 1 minute.

The above developer was tested in a device using an organic photoreceptor containing a trigonal selenium photogenerating layer, and coated thereover a charge transport lever of N,N'-diphenyl-N,N'-bis(3-methyl phenyl)-1,1'-biphenyl-4,4'-diamine, reference U.S. Pat. No. 4,265,990, which was negatively charged, and the Viton fuser of Example VI. Good quality prints with high solid area density and low background density were obtained. The Viton fuser was not noticeably affected.

The stearyl dimethyl phenethyl ammonium para-toluene sulfonate prepared in accordance with Example I, was placed on a part of a Viton fuser roll, lead oxide, duPont Viton E-430 and heated to 205° C. for 30 minutes. The Viton fuser roll was then washed with alcohol to remove the compound and the roll was examined for discoloration and cracks. The Viton fuser roll did not discolor, nor turn black, nor were any surface cracks observed, indicating that stearyl dimethyl phenethyl ammonium para-toluene sulfonate was compatible with the Viton fuser.

EXAMPLE IX

A toner comprising 2 percent by weight of the stearyl dimethyl phenethyl ammonium para-toluene sulfonate prepared in accordance with Example I, 20 percent of Mapico Black magnetite pigment commercially available from Cites Services Co., and 78 percent by weight of a styrene/n-butylmethacrylate resin 58/42, 58 weight percent styrene, 42 percent n-butylmethacrylate, was fabricated by melt blending followed by mechanical attrition. The toner was further classified to remove particles smaller than 5 microns. The triboelectric charge of this toner against the carrier described in Example VI at 3 percent toner concentration are given below:

| Time | Toner Tribo uc/g (microcoulombs per gram) |
|---|---|
| 10 minutes | +31 |
| 1 hour | +24 |
| 4 hours | +21 |
| 24 hours | +15 |

Charge distribution measurements showed that the above developer had a narrow charge distribution, with a minimum insignificant number, less than 1 percent of toner particles, containing a low charge, less than +15 uc/g, and minimum wrong sign negatively charged toner particles. Admix experiments showed that the toner had fast charging properties when fresh uncharged toner was added to the developer, that is, the fresh toner became positively charged in less than 1 minute.

The toners and developers of the present invention are useful for causing the development of images in electrophotographic systems as indicated herein. In one imaging method there is form a negative electrostatic latent image on the photoreceptor surface, followed by containing the image with the dry positively charged developing compositions of the present invention. Subsequently, the developed latent image can be transferred to a substrate, such as paper, and optionally permanently fixed thereto by heat.

The triboelectric charges shown were determined by the known Faraday Cage technique.

Other modifications of the present invention may occur to those skilled in the art based upon a reading of the disclosure of the present application and these modifications are intended to be included within the scope of the present invention.

I claim:

1. The compound stearyl dimethyl phenethyl ammonium para-toluene sulfonate.

* * * * *